United States Patent [19]
Kozawa et al.

[11] Patent Number: 5,335,648
[45] Date of Patent: Aug. 9, 1994

[54] ENTOPTOSCOPIC INSTRUMENT FOR OBSERVING THE INTERIOR OF AN EYE

[75] Inventors: Tadahiko Kozawa, Ibaragi; Yasuhiro Osakabe; Takashi Suematu, both of Tokyo, all of Japan

[73] Assignee: Hoya Corporation, Tokyo, Japan

[21] Appl. No.: 38,501

[22] Filed: Mar. 29, 1993

[30] Foreign Application Priority Data

Apr. 30, 1992 [JP] Japan .............................. 4-036291[U]

[51] Int. Cl.$^5$ ................................................ A61B 3/00
[52] U.S. Cl. .......................................... 128/6; 128/22; 128/23; 362/32; 362/138
[58] Field of Search ................... 128/23, 6, 22, 4, 21; 362/138, 32; 385/119

[56] References Cited

U.S. PATENT DOCUMENTS 4,870,952 10/1989 Martinez ................................ 128/23
4,878,487 11/1989 Sinnett .................................. 128/23

*Primary Examiner*—Richard J. Apley
*Assistant Examiner*—John Mulcahy
*Attorney, Agent, or Firm*—Ladas & Parry

[57] ABSTRACT

An entoptoscopic instrument (10) comprises a light source unit (20), a light transmitting member (30), and a mirror member (40). The light source unit (20) comprises a filter for cutting off harmful wavelength components from illumination light to restrict the wavelength components of the illumination light to a range between 440 nm and 880 nm.

6 Claims, 6 Drawing Sheets

ENTOPTOSCOPIC INSTRUMENT FOR OBSERVING THE INTERIOR OF AN EYE

BACKGROUND OF THE INVENTION

This invention relates to an entoptoscopic instrument for observing the interior of an eye and, in particular, to an entoptoscopic instrument for use in intraocular lens implant surgery, It is a recent trend that cataract surgery and intraocular lens implant surgery have been widely performed. This also brings about a considerable increase in the frequency of secondary implant of an intraocular lens and fixation of a loop of the intraocular lens to the ciliary sulcus. It is to be noted that the ciliary sulcus is situated at the rear the iris and is not directly visible during such surgery. Hence, the intraocular lens must be fixed to the ciliary sulcus without it being visible. In this connection, an expert technique is required to fix the loop and to pass a needle. At present, it is a general practice to also perform peripheral iridectomy on such fixation or to use an endoscope. However, if the peripheral iridectomy is additionally performed, an extra operation is required by the surgeon. On the other hand, when the endoscope is used, the surgeon must monitor a display device located at a position completely different from the part which is operated, during a surgical operation. This adds to the burden imposed on the surgeon.

In Japanese Utility Model Prepublication No. 19106/1984, a dental observation mirror which has a lamp has been proposed and is generally called a "dental mirror". However, this mirror is not suitable for ophthalmological surgery due to its size and luminous energy.

On the other hand, dental stomatoscopes with an illuminator have been proposed in Japanese Utility Model Publications Nos. 22477/1978 and 22478/1978. In both of the dental stomatoscopes, light is emitted from an external light source and guided through a fiberscope (optical fiber) to illuminate a desired part. The light source is generally composed of a halogen lamp. The halogen lamp has a spectral characteristic spreading over a wide wavelength range from an ultraviolet region to infrared region.

If illumination light emitted from the halogen lamp is used in ophthalmologic surgery, an ophthalmic defect is undesirably produced in the eye due to the particular wavelength components of, for example, less than 440 nm contained in the illumination light.

For example, consideration will be directed to a patient of aphakia whose eye lacks a crystalline lens after cataract surgery is performed. It is noted here that such a crystalline lens in a normal eye serves to prevent wavelength components in the ultraviolet band from arriving onto the retina and to reduce the amount of wavelength components which arrives on the retina in a visible violet-blue band.

In the case of the aphakia patient, the ultraviolet and visible violet-blue wavelength components directly arrive on a retina through the eye of the aphakia patient without any substantial reduction. This gives rise to an abnormal condition or damage of a retinal cell which may be called retinal damage by blue light. In addition, the infrared components could cause thermal degeneration to occur in ophthalmic tissue.

SUMMARY OF THE INVENTION

It is therefore an object of this invention to provide an entoptoscopic instrument which is capable of reducing the physical demand imposed upon the surgeon during surgery to thereby facilitate the surgery.

It is another object of this invention to provide an entoptoscopic instrument of the type described, which is capable of preventing occurrence of an ophthalmic defect of a patient to thereby improve safety.

An entoptoscopic instrument according to this invention comprises a light source unit for generating illumination light, a light transmitting member having an incoming end and an outgoing end for guiding the illumination light from the incoming end to the outgoing end to produce the illumination light through the outgoing end along an optical axis, a mirror member having a mirror surface and arranged at the outgoing end of the light transmitting member so that the mirror surface forms an intersecting angle between 15° and 45° with respect to the optical axis, and at least one filter located in an area between the light source unit and the outgoing end of the light transmitting member to remove harmful wavelength components from the illumination light.

With the above-mentioned structure, at least one sort of the filters is operable to substantially completely cut off, from the illumination light generated by the light source unit, the wavelength components which might be harmful to retinal cells. Such harmful wavelength components fall within a wavelength region (the ultraviolet region and the visible violet-blue region) shorter than 440 nm and another region (the infrared region) longer than 1000 nm. As a result, it is possible to provide the entoptoscopic instrument which is capable of preventing occurrence of ophthalmic damage and which can therefore improve safety.

As described above, the mirror member having a mirror surface is arranged at the outgoing end of the light transmitting member so that the mirror surface forms the intersecting angle between 15° and 45° with respect to the optical axis. Thus, it is possible to reflect a desired part in an eye on the mirror surface and to transmit through the cornea a resultant reflected image which is then observed by the surgeon during surgery. Accordingly, the operator need not monitor a display unit remote from a part to be operated during a surgical operation. This enables reduction of the physical demand imposed upon the surgeon.

DESCRIPTION OF THE PREFERRED EMBODIMENT

Figure 1:
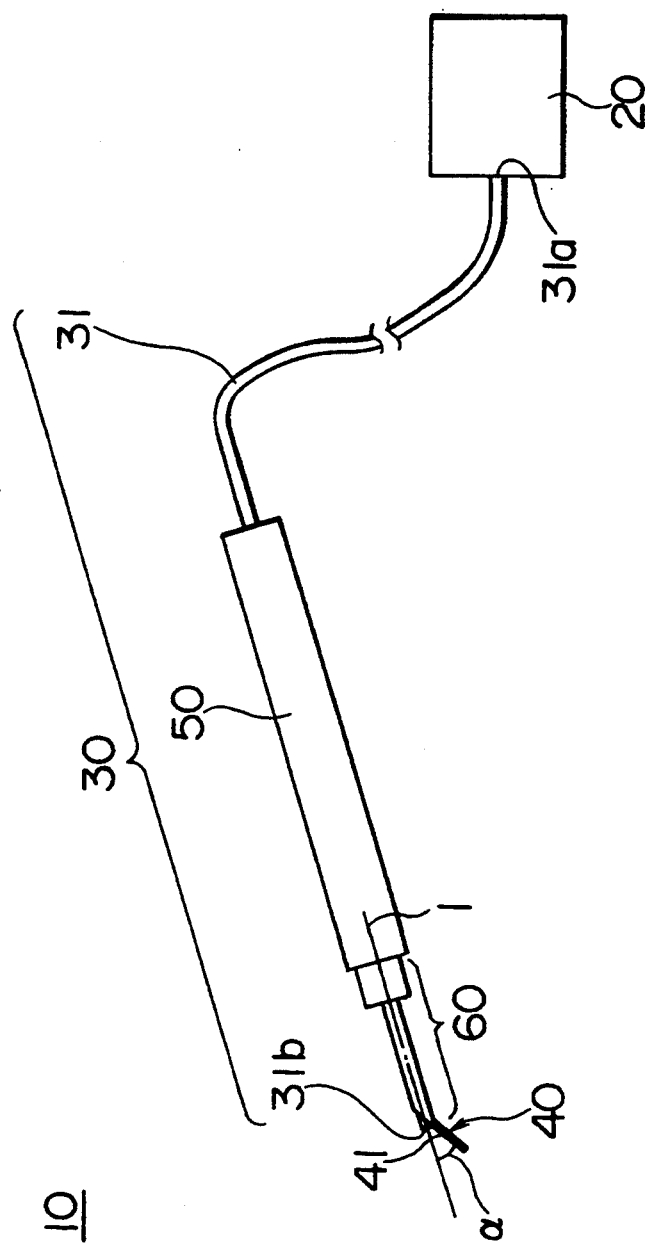
FIG. 1 is a schematic diagram of an entoptoscopic instrument according to a first embodiment of this invention.

Now, description will be made as regards an embodiment of this invention with reference to the drawing.

Referring to FIG. 1, an entoptoscopic instrument 10 according to a first embodiment of this invention essentially comprises a light source unit 20 for generating illumination light, a light transmitting member 30 for transmitting the illumination light, and a mirror member 40 for receiving reflected light.

More specifically, the light transmitting member 30 comprises an optical guide 31 having an incoming end 31a and an outgoing end 31b. The illumination light generated by the light source unit 20 is incident through the incoming end 31a and radiated from the outgoing end 31b along an optical axis 1. Thus, the optical guide 31 serves as a light transmission path for guiding the illumination light. The light transmitting member 30 further comprises a handpiece 50 to be held by an operator and a mirror connector 60 for connecting the handpiece 50 and the mirror member 40 adjacent to the handpiece 50.

The illustrated optical guide 31 is extended through the handpiece 50 and the mirror connector 60 without separation of the optical guide 31. The outgoing end 31b of the optical guide 31 is kept in contact with the mirror member 40.

The mirror member 40 is arranged at the outgoing end 31b to form an intersecting angle α between 15° and 45° with respect to the optical axis 1. The mirror member 40 has a mirror surface 41. The mirror surface 41 is an inner surface facing within the intersecting angle α and the mirror 40 is attached to the outgoing end 31b at an angle so that as the mirror surface 41 extends away from the outgoing end and 31b its distance from the optical axis increases as shown in FIG. 1.

In the example being illustrated, the optical guide 31 is formed by a single optical fiber which has the same diameter from the incoming end 31a to the outgoing end 31b. Therefore, the optical guide 31 is very simple in structure and can avoid an attenuation which might occur on connection of a plurality of optical fibers.

Figure 2:
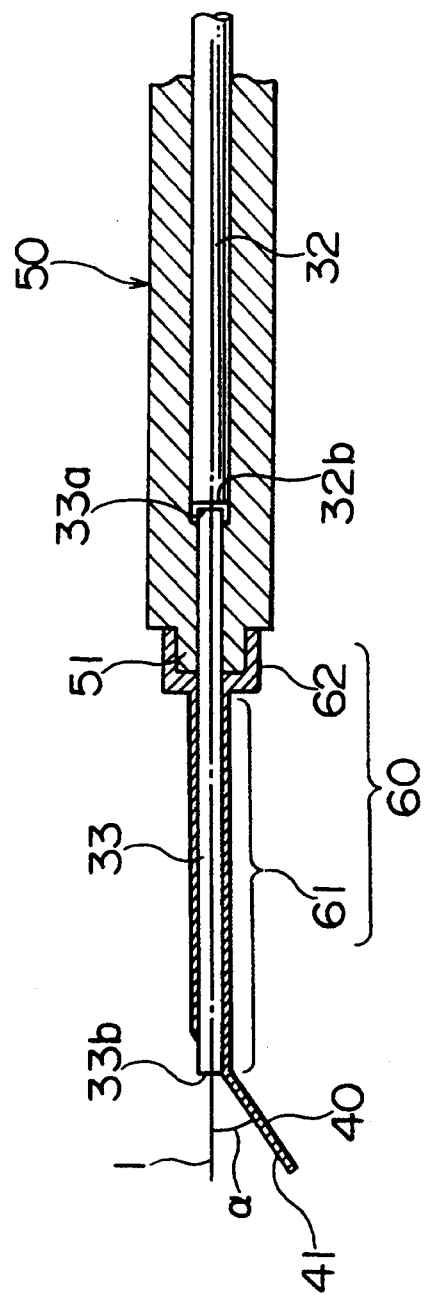
FIG. 2 is an enlarged sectional view of a main part of an entoptoscopic instrument according to a modification of the first embodiment illustrated in FIG. 1.

Referring to FIG. 2, illustration is made of a modification of the entoptoscopic instrument shown in FIG. 1. The illustrated optical guide 31 comprises a first optical guide 32 and a second optical guide 33 having a diameter smaller than that of the first optical guide 32, as illustrated in FIG. 2. The first optical guide 32 has an incoming end (not shown in FIG. 2) like in FIG. 1 and an emitting end 32b. Likewise, the second optical guide, 33 has an incident end 33a and an outgoing end 33b. Inside the handpiece 50, the first and the second optical guides 32 and 33 are close to each other, with the emitting end 32b faced to the incident end 33a.

It is readily understood that the incoming end 32a of the first optical guide 32 and the outgoing end 33b of the second optical guide 33 may be made to correspond to the incoming end 31a and the outgoing end 31b of the optical guide 31 shown in FIG. 1, respectively.

In FIG. 2, the mirror connector 60 has a mirror-side portion 61. The mirror-side portion 61 and the mirror member 40 are inserted into an eyeball and operated therein. In this connection, the mirror-side portion 61 of the mirror member 60 preferably has an outer diameter between 0.5 mm and 2.5 mm while the second optical guide 33 preferably has a diameter between 0.25 mm and 1.5 mm.

The handpiece 50 has a handpiece end 51 while the mirror connector 60 has a connector end 62. As illustrated in FIG. 2, the mirror connector 60 is detachably screwed into the handpiece 50 with a threaded engagement between the handpiece end 51 and the connector end 62.

In FIG. 2, the handpiece end 51 of the handpiece 50 has male threads while the connector end 62 of the mirror connector 60 has female threads. However, it will be understood that the threaded engagement of the handpiece end 51 and the connector end 62 can be reversed relative to that illustrated in FIG. 2. In addition, the handpiece 50 and the mirror connector 60 may be united with each other. To facilitate manipulation or handling by the surgeon, the handpiece 50 preferably has an outer diameter between 4.0 mm and 15.0 mm, more preferably, between 6.0 mm and 9.0 mm.

In view of easiness of the handling, it is desirable that the mirror member 40 and the mirror connector 60 are not transformed or deformed in shapes during operation. In this connection, the mirror member 40 and the mirror connector 60 are preferably made of a material having a sufficient stiffness. For example, the material may be selected from a group consisting of metals, resins, and ceramics. In view of the safety for contact with a living body, a biocompatible metal, such as stainless steel, is preferable. In order to form the mirror surface 41, the mirror member 40 is subjected to polishing or mirror finish. Alternatively, the mirror surface 41 may be preliminarily prepared separately from the mirror member 40 and may thereafter be attached to the mirror member 40.

The mirror member 40 and the mirror connector 60 may be integrally formed or may be formed as separate components which are attached together. Since the mirror member 40 and the mirror connector 60 are detachably connected to the handpiece 50 as described above, various treatments, such as washing and sterilization, can be readily performed. If necessary, the mirror member 40 and the mirror connector 60 may be made disposable. Thus, the instrument is remarkably advantageous in safety and sanitary aspects. Furthermore, utility can be increased by preparing a wide variety of exchangeable mirror members 40 and/or mirror connectors 60. For example, variable sizes of the instruments and/or variable intersecting angles α of the instruments (namely, the intersecting angle α between the mirror member 40 and the optical axis 1 of the illumination light emitted from the second optical guide 33 of the light transmitting member) may be selected so as to respond to various requirements.

As mentioned before, the optical guides 31 and 32 in FIGS. 1 and 2 may be formed by a single one of flexible optical fiber cables which may be used in general. Preferably, such an optical fiber has a reduced transmission loss and is covered with a coating material having a high durability. For example, each of the optical guides 31 and 32 comprises a polyethylene-coated single-core plastic fiber cord and has an outer diameter of 2.2 mm and a fiber diameter between 0.75 mm and 1 mm.

Description will now proceed to the light source unit 20.

Figure 3:
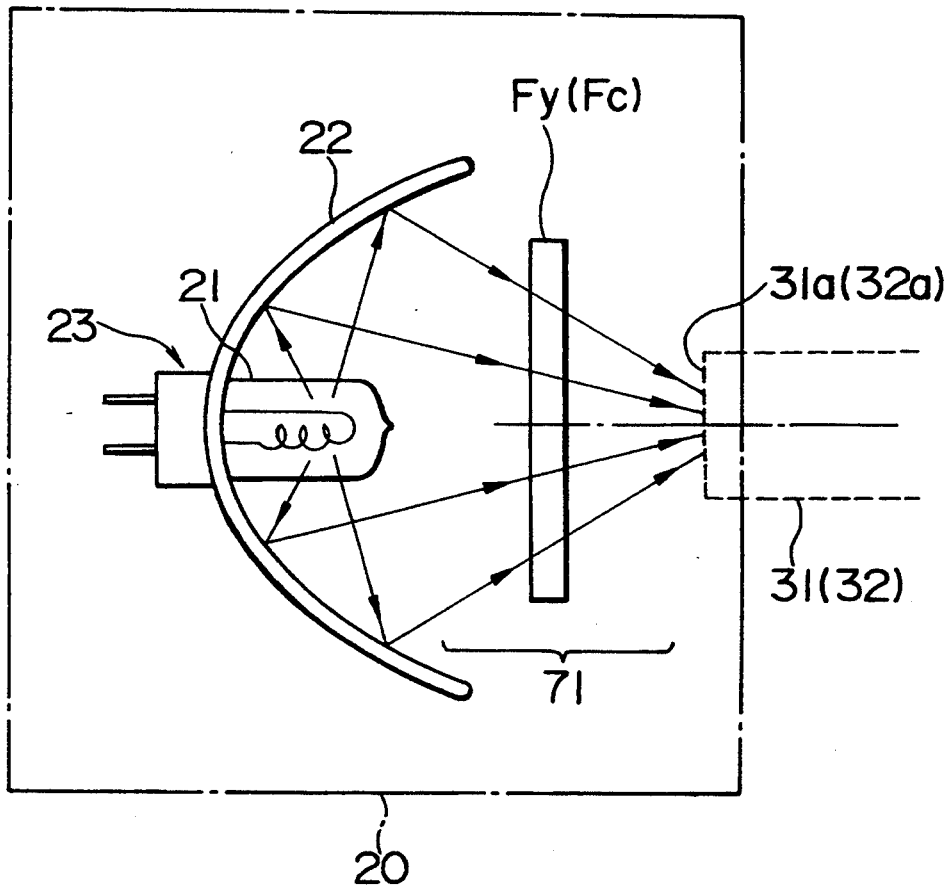
FIG. 3 is a schematic diagram of a light source unit in the entoptoscopic instruments illustrated in FIGS. 1 and 2.

Referring to FIG. 3, the light source unit 20 essentially comprises a halogen lamp 21 and a mirror 22. A combination of the halogen lamp 21 and the mirror 22 forms a halogen lamp/mirror assembly 23. The mirror 22 generally comprises an ellipsoidal mirror. Alternatively, the mirror 22 may comprise a dichroic mirror having a heat ray filtering characteristic. Light generated by the halogen lamp 21 is reflected by the mirror 22 to be converged and then incident into the optical guide 31 (32) through the incoming end 31a (32a) connected to the light source unit 20, as shown in FIG. 3.

A special effect is accomplished by arranging at least one filter in an area 71 between the mirror 22 and the incoming end 31a (32a) of the optical guide 31 (32). With this structure, the filter serves to cut off harmful wavelength components contained in the illumination light generated by the light source unit 20. For example, a heat ray absorption filter Fc satisfies the following conditions:

| |
|---|
| when 400 nm $\leq \lambda \leq$ 580 nm, T $\geq$ 60%, |
| when $\lambda$ = 600 nm, T $\geq$ 55%, |
| when $\lambda$ = 700 nm, T $\geq$ 30%, |
| when $\lambda$ = 800 nm, T $<$ 30%, |
| when $\lambda \geq$ 880 nm, T $<$ 10%, | where $\lambda$ represents the wavelength and T represents the transmissivity. When the heat ray absorption filter Fc is located in the area 71, it is possible to substantially completely cut off, from the illumination light emitted from the outgoing end 31b (33b) of the optical guide 31 (33), wavelength components within a range longer than 1000 nm in an infrared region. It will be understood here that the expression "substantially completely cut" does not mean the state where no transmission is allowed at all (the transmissivity is equal to 0%) but represents the state where transmission is too small (the transmissivity is equal to several percent) to cause any defect in an ophthalmic tissue as a heat ray.

On the other hand, a yellow filter Fy satisfies the following conditions representing the relationship between the wavelength $\lambda$ and the transmissivity T:

| |
|---|
| When $\lambda <$ 440 nm, T $<$ 1% |
| When $\lambda$ = 480 nm, T $\geq$ 30% |
| When 500 nm $\leq \lambda \leq$ 750 nm, T $\geq$ 85%. |

When the yellow filter Fy is located in the area 71, it is possible to cut, from the illumination light emitted through the outgoing end 31b (33b) of the optical guide 31 (33), ultraviolet and visible violet-blue components within a range shorter than 440 nm.

Since the heat ray absorption filter Fc is operable to substantially completely transmit visible light, no trouble is caused when it is used in the entoptoscopic instrument according to this invention. On the other hand, the yellow filter Fy has a visible light transmission characteristic which does not cause any problem when it is used in the entoptoscopic instrument according to this invention.

Use may be made of a combination of the above-mentioned two types of the filters.

In this event, the relationship between the wavelength $\lambda$ of the illumination light and the transmissivity T is represented by:

| |
|---|
| when $\lambda <$ 440 nm, T $<$ 1%, |
| when $\lambda$ = 480 nm, T $\geq$ 30%, |
| when 500 nm $\leq \lambda \leq$ 580 nm, T $\geq$ 60%, |
| when $\lambda$ = 600 nm, T $\geq$ 55%, |
| when $\lambda$ = 700 nm, T $\geq$ 30%, |
| when $\lambda$ = 800 nm, T $<$ 30%, |

| -continued |
|---|
| when $\lambda \geq$ 880 nm, T $<$ 10%. |

Thus, it is readily possible to selectively transmit the wavelength components of the illumination light within a range which is not shorter than 440 nm and which is shorter than 880 nm. The size of the filter can be adjusted so that the filter can be located at any position between the incoming end 31a (32a) of the optical guide 31 (32) and the outgoing end 31b (33b) of the optical guide 31 (33).

Practially, the above-mentioned heat ray absorption filter Fc may be a glass type composed, for example, of HA-20, HA-30, and HA-50 which exhibit transmissivities of 20%, 30%, and 50% at the wavelength of 750 nm, respectively, and which are commercially manufactured and sold by HOYA Corporation, Tokyo, Japan. The heat ray absorption filter will be specified by Fc (HA-50) or so. On the other hand, the above-mentioned yellow filter Fy may be a sharp cut filter (yellow) of a glass type formed by glass sold by HOYA Corporation in the trade name of Y-46 and Y-48. Such filters have transmission cutoff wavelengths of 460 nm and 480 nm and will be depicted at Fc (Y-46) or so.

Figure 4:
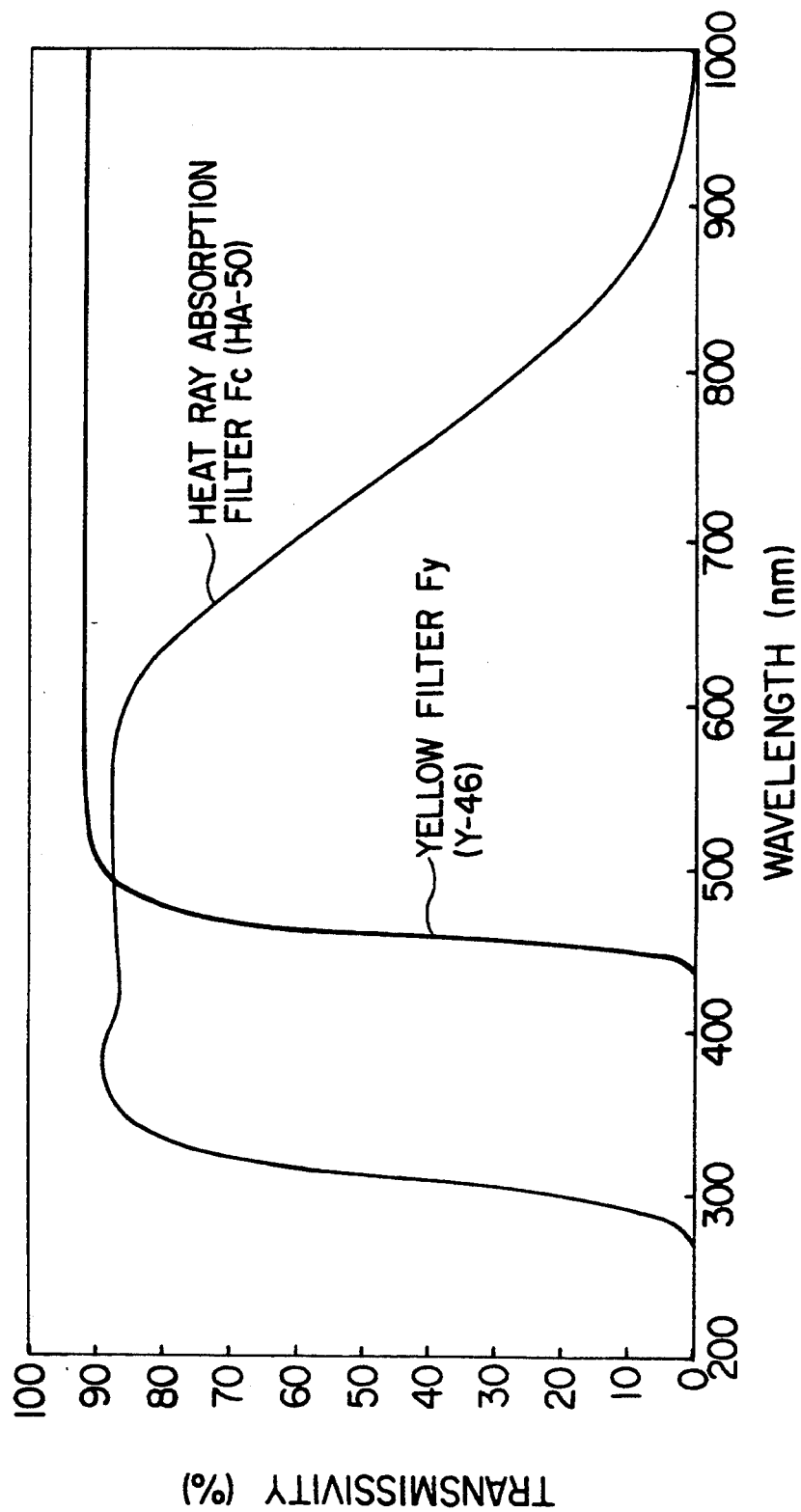
FIG. 4 shows light transmission characteristics of a filter illustrated in FIG. 3.

Referring to FIG. 4, light transmission characteristics are shown as regards the heat ray absorption filter Fc (HA-50) and the yellow filter Fy (Y-46). In the figure, the abscissa and ordinate represent a wavelength ($\lambda$) and transmissivity (T), respectively. As is readily understood from FIG. 4, the yellow filter Fy (Y-46) is effective to cut off the wavelength shorter than 400 nm and to pass the wavelength longer than 500 nm. On the other hand, the heat ray absorption filter Fc (HA-50) is helpful to transmit a wavelength region between 300 nm and 700 nm. Therefore, a combination of the yellow filter Fy (Y-46) and the heat ray absorption filter Fc (HA-50) serves to pass the wavelength region between 500 nm and 700 nm and will be called a filter unit.

Figure 5:
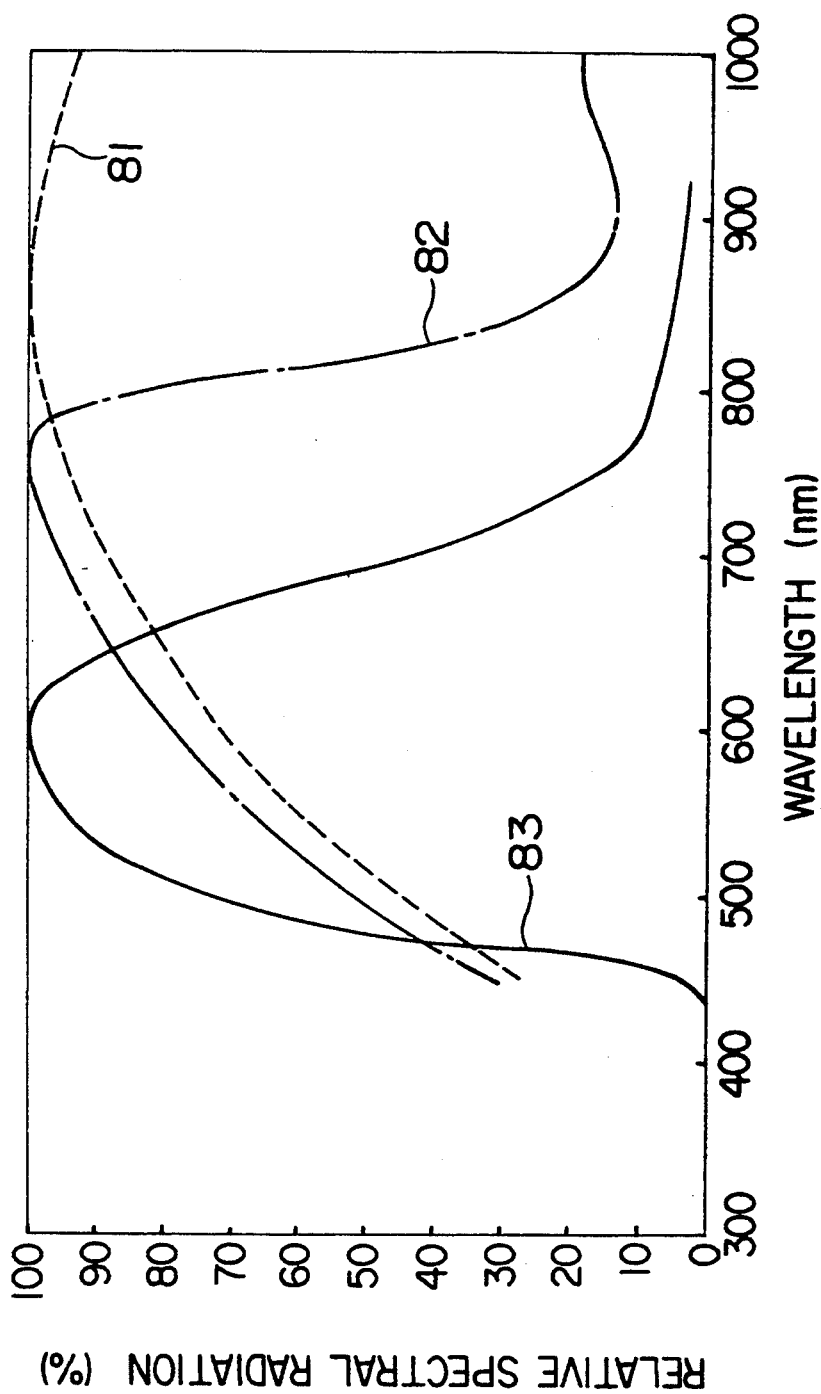
FIG. 5 shows emission spectra of a halogen lamp illustrated in FIG. 3.

Referring to FIG. 5, illustration is made regarding the relationship between an emission spectrum of the halogen lamp 23 (FIG. 3) and a spectrum of the filter unit illustrated in FIGS. 3 and 4. In FIG. 5, a broken line curve 81 represents the emission spectrum of the halogen lamp while a dash-and-dot line curve 82 represents the emission spectrum of the halogen lamp with a dichroic mirror. A solid line curve 83 represents the light transmission characteristic of the filter unit which comprises the heat ray absorption filter Fc (HA-50) and the yellow filter Fy (Y-46), as mentioned in conjunction with FIG. 4. At any rate, the emission spectrum of either the halogen lamp or the halogen lamp with the dichroic mirror is restricted to a passband of the filter unit which is ranged between 500 nm and 700 nm.

Alternatively, the heat absorption filter Fc may be replaced by a near-infrared ray cut filter (ICF) which comprises vacuum deposition films. The near-infrared ray cut filter (ICF) is formed by depositing a desired number of dielectric transparent films on a surface of a glass substrate by means of vapor deposition. When the heat ray absorption glass filter is used as the substrate, the near-infrared ray cut filter (ICF) can substantially completely cut off the wavelength components within a range longer than 700 nm (specifically, only 10% of transmission is passed at the wavelength of 880 nm or so) while visible light is not substantially absorbed. Accordingly, such near-infrared ray cut filter is extremely effective. Specifically, use may be made of ICF/HA30 Glass and ICF/HA50 Glass (for example, these products are commercially sold by HOYA Corporation) and formed by heat absorption filters (HA-30 and HA-50) having a plurality of vapor deposition films deposited thereon, respectively.

As described previously herein, a serious problem could be caused to occur in the case where the illumination light generated from the halogen lamp is used in ophthalmologic surgery. Accordingly, the entoptoscopic instrument according to this invention is advantageous in that the harmful wavelength components contained in the illumination light are effectively cut off by the use of the filter.

It is noted that the halogen lamp used in the foregoing embodiment may be replaced by a metal halide lamp or a xenon lamp.

Next, description proceeds to the operation of the entoptoscopic instrument 10 according to this invention.

Figure 6:
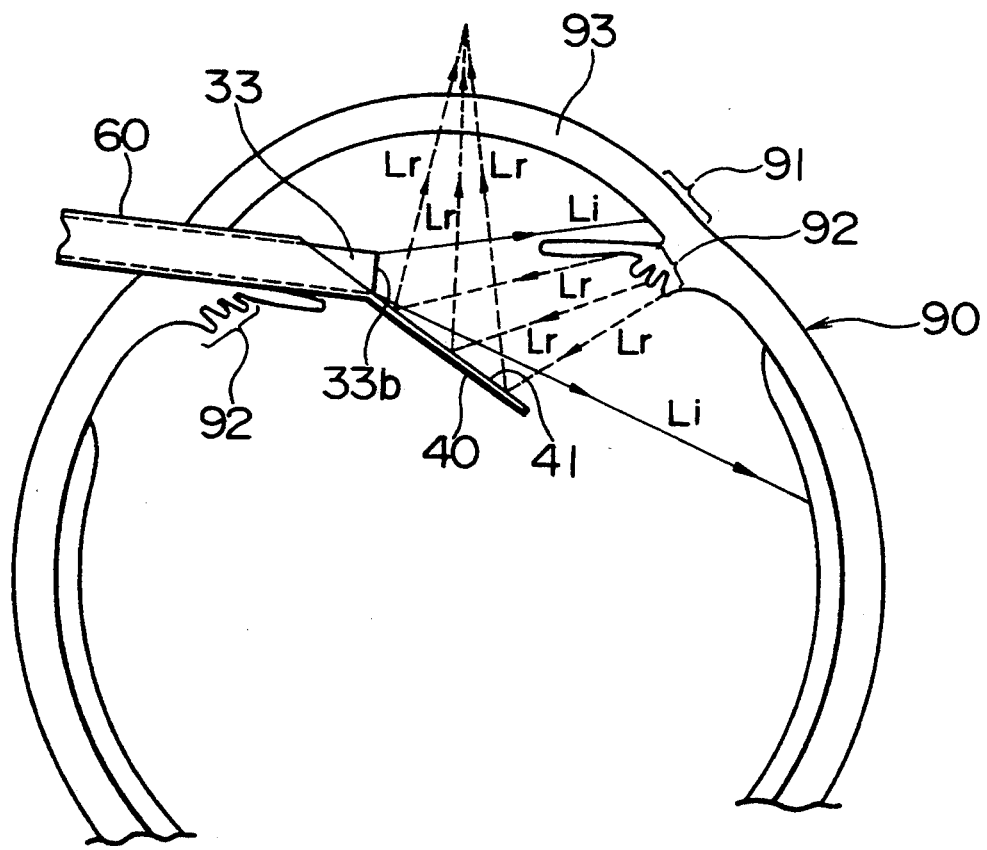
FIG. 6 is a view for describing the operation of the entoptoscopic instruments illustrated in FIGS. 1 and 2.

Referring to FIG. 6, the surgeon inserts the mirror member 40 and the mirror connector 60 of the entoptoscopic instrument 10 into an eye ball 90 through an incised part in a corneal ring 91. The illumination light generated by the light source unit 20 is emitted through the outgoing end 33b of the optical guide 33 as emitted light Li. The emitted light Li illuminates the ciliary sulcus 92 of the eyeball 90 and any other desired part. Reflected light Lr from the ciliary sulcus 92 is reflected on the mirror surface 41 of the mirror member 40 and then emitted through a cornea 93 to the outside of the eyeball 90. Thus, the reflected light Lr can be readily observed by the surgeon through a microscope (not shown).

As thus far been described, the entoptoscopic instrument according to this invention has an excellent manipulatability and therefore reduces physical demand imposed upon the surgeon. In addition, the entoptoscopic instrument has an illuminance sufficient to perform a surgical operation and is still capable of preventing occurrence of an ophthalmic defect of the patient. Thus, the entoptoscopic instrument achieves an improved safety.

Accordingly, the entoptoscopic instrument according to this invention is very effective.

While this invention has thus far been described in conjunction with a preferred embodiment thereof, it will readily be possible for those skilled in the art to put this invention into practice in various other manners. As regards the material, the shape, and the arrangement of the mirror, it has been confirmed that three kinds of mirrors can be used. Such a mirror may be made of metal (stainless steel of Japanese Industrial Standard JIS300 series) generally used in various surgical instruments. Another one of the mirror may be made of biocompatible metal (platinum) or plastics (PMMA) generally used as an intraocular lens and was coated with metal (platinum). In any event, the mirrors may be subjected to mirror finish by a special polishing process, such as buffing. The respective mirrors may be shaped into a circle or a rectangle chamfered at corners. Each diameter of the mirrors may be approximately equal to 3 mm.

According to the inventor's experimental studies, it has been found that, among those mirrors, the mirror made of PMMA and coated with metal has been the best one for easy observation by the operator. The other mirrors made of stainless steel and platinum also exhibited the satisfiable results. Since these results have been supposed to be affected by the finishing conditions of the mirror surfaces, three kinds of the mirrors were deemed to be equivalent.

As regards the platinum-coated mirror, removal of the coating film and elution of metal could be caused to occur. Accordingly, the platinum-coated mirror is not adapted for practical use. In addition, platinum is a material which is very expensive. In this connection, the platinum mirror is not adapted for practical use.

Both the circular shape and the rectangular shape exhibited the satisfactory results. In order to facilitate manufacture, the rectangular shape is preferable. However, it is necessary to pay great attention in a finishing process so as not to injure the ophthalmic tissue during insertion into the eye. Observation was satisfactorily carried out with the mirror having the diameter of 3 mm or so.

To facilitate insertion into the eye as well as observation, the mirror is desirably arranged at an intersecting angle between 20° and 40°. If the intersecting angle is acute, observation over a wide range is possible. However, the angle is preferably equal to 30° or so in a normal use.

What is claimed is:

1. An entoptoscopic instrument for use in observing living tissue in a patient, said entoptoscopic instrument comprising:

a light source unit for generating illumination light;

a light transmitting member having an incoming end and an outgoing end for guiding said illumination light from said incoming end to said outgoing end to produce said illumination light through said outgoing end along an optical axis; and a mirror member having a mirror surface and arranged at said outgoing end of said light transmitting member so that said mirror surface is inclined with respect to the optical axis at an angle between 15° and 45° with said mirror surface facing towards said optical axis and increasing in distance from said optical axis as the mirror surface extends from said outgoing end of the light transmitting member; and filter means located in an area between said light source unit and said outgoing end of said light transmitting member for attenuating wavelength components from said illumination light which can damage said living tissue.

2. An entoptoscopic instrument is claimed in claim 1, wherein said filter means has a filter characteristic which passes wavelength components within a range between 440 nm and 880 nm.

3. An entoptoscopic instrument as claimed in claim 1, wherein said filter means satisfies the following conditions:

--- when $400 \text{ nm} \leq \lambda \leq 580 \text{ nm}$, $T \geq 60\%$,
when $\lambda = 600 \text{ nm}$, $T \geq 55\%$,
when $\lambda = 700 \text{ nm}$, $T \geq 30\%$,
when $\lambda = 800 \text{ nm}$, $T < 30\%$, and
when $\lambda \geq 880 \text{ nm}$, $T < 10\%$,

--- where $\lambda$ represents the wavelength the T represents the transmissivity.

4. An entoptoscopic instrument as claimed in claim 1, wherein said filter means includes a plurality of filters at least one of which satisfies the following conditions:

when λ < 440 nm, T < 1%,
when λ = 480 nm, T ≧ 30%, and
when 500 nm ≦ λ ≦ 750 nm, T ≧ 85%, where λ represents the wavelength and T represents the transmissivity.

5. An entoptoscopic instrument as claimed in claim 1, for observing the interior of an eye, said filter means having a filter characteristic to transmit illumination light therethrough in a restricted wavelength range which will not damage the living tissue of the eye of the patient.

6. An entoptoscopic instrument as claimed in claim 1, wherein the wavelength components which are damaging to said living tissue and which are attenuated by said filter means are wavelengths shorter than 440 nm and longer than 1000 nm.

* * * * *